United States Patent [19]

Su et al.

[11] Patent Number: 5,070,166
[45] Date of Patent: Dec. 3, 1991

[54] WETTABLE, FLEXIBLE, OXYGEN PERMEABLE, CONTACT LENS CONTAINING POLYOXYALKYLENE BACKBONE UNITS, AND USE THEREOF

[76] Inventors: Kai C. Su, 13090 Hopewell Rd., Alpharetta, Ga. 30201; Frank Molock, 1535 Summer Hollow Trail, Lawrenceville, Ga. 30245

[21] Appl. No.: 418,687

[22] Filed: Oct. 2, 1989

Related U.S. Application Data

[63] Continuation of Ser. No. 315,225, Feb. 23, 1989, abandoned, which is a continuation of Ser. No. 160,622, Feb. 26, 1988, abandoned.

[51] Int. Cl.$^5$ .................. C08F 26/02; C08L 71/02; G01B 1/04
[52] U.S. Cl. .................. 526/301; 525/404; 525/455; 523/106; 351/160 H
[58] Field of Search .................. 523/106; 526/301; 525/404, 455; 351/160 H

[56] References Cited

U.S. PATENT DOCUMENTS

| | | | |
|---|---|---|---|
| 3,894,131 | 7/1975 | Speech | 521/159 |
| 3,985,688 | 10/1976 | Speech | 521/116 |
| 4,192,827 | 3/1980 | Mueller et al. | |
| 4,315,703 | 2/1982 | Gasper | 524/507 |
| 4,684,558 | 8/1987 | Keusch et al. | 428/220 |
| 4,752,627 | 6/1988 | Froix | 323/106 |
| 4,780,488 | 10/1988 | Su et al. | |
| 4,857,606 | 8/1989 | Su et al. | |
| 4,859,780 | 8/1989 | Molock et al. | |
| 4,921,956 | 5/1990 | Molock et al. | |

*Primary Examiner*—Allan M. Lieberman

[57] ABSTRACT

Contact lenses which are optically clear, wettable, flexible, and of high oxygen permeability in the aqueous ocular environment of use, of a polymer containing polyoxyalkylene backbone units are disclosed, as well as the preparation thereof and methods of treating vision defects therewith.

14 Claims, No Drawings

WETTABLE, FLEXIBLE, OXYGEN PERMEABLE, CONTACT LENS CONTAINING POLYOXYALKYLENE BACKBONE UNITS, AND USE THEREOF

This is a continuation of application Ser. No. 315,225, filed on Feb. 23, 1989, now abandoned, which in turn is a continuation of application Ser. No. 160,622, filed on Feb. 26, 1988, now abandoned.

BACKGROUND OF THE INVENTION

1. Field of the Invention

This invention relates to opthalmic devices, such as contact lenses and intraocular implants, and particularly contact lenses of a polymer containing a backbone containing polyoxyalkylene units possessing a unique blend of properties including a) high oxygen permeability, b) good wettability, c) flexibility, and d) optical clarity in the ocular environment of use.

2. Background of the Invention

The use of optical contact lenses for the correction of vision defects or for cosmetic purposes is well known. However existing contact lenses have been found to be unacceptable to many potential contact lens patients for a variety of reasons. For example, early contact lenses were made from polymethyl methacrylate (PMMA). While PMMA lenses have high optical clarity and good durability, they are rigid lenses possessing low oxygen permeability. Consequently, PMMA lenses may result in eye irritation and corneal oxygen deprivation leading to wearer intolerance and limiting the usefulness of such lenses.

In an attempt to avoid these problems, so-called "soft" lenses, capable of swelling in an aqueous environment, were developed. These "soft" or hydrogel lenses, characteristically made from poly (2-hydroxyethyl methacrylate), poly (vinyl alcohol) or poly (vinylpyrrolidone) generally result in less irritation and intolerance than PMMA lenses for most patients. When substantial amounts of water are absorbed into the hydrogel, the oxygen permeability is increased over that of PMMA lenses, and the flexibility of such hydrogel lenses is high, thereby increasing patient comfort. However, the oxygen permeability of such hydrogel lenses is generally still rather low, and the durability is poor. Moreover, due to the high water content of such lenses, they generally have a tendency to collect and trap proteinaceous and other tear fluid materials, resulting in lens clouding over a period of time.

In another attempt to solve problems associated with early lenses, silicone, or siloxane, rubber lenses were developed. They are advantageous in that they possess high oxygen permeability and an aesthetically appealing texture when worn. However, due evidently to the generally low thermal conductivity of silicone rubber, burning sensations in wearers of silicone rubber lenses have been reported. Also, as silicone lenses tend to be lipophilic, such lenses may tighten onto the cornea, trapping debris between the lens and cornea, thereby resulting in corneal abrasions. Also, due to the characteristic lipophilic nature of such lenses, the silicone rubber is mucophilic and non-wettable, attracting ocular debris such as proteins, lipids, mucoids and the like.

It is an object of the present invention to overcome these and other disadvantages of the art by providing substantially siloxane free, wettable, oxygen permeable, ophthalmic devices, such as contact lenses and corneal implants, of a polymer containing polyoxyalkylene backbone units.

A further object of the invention is to provide a method of correcting visual defects in the form of refractive errors by fitting to the patient's eye in need of the same, a corrective contact lens of such polymer.

These and other objects of the invention are apparent from the following detailed description of the invention.

DETAILED DESCRIPTION

One embodiment of the present invention relates to an optically clear, hydrolytically stable, biologically inert, wettable and flexible, substantially siloxane free, non-swellable in aqueous ocular tear fluid, oxygen permeable ophthalmic device, such as a contact lens, fabricated from a polymer containing segments of the formula $$[\text{-A-L-D-}]_w \qquad (I)$$

each A is a copolymeric block of polyoxyalkylene. Preferably at least 30%, more preferably at least 50%, still more preferably at least 75%, most preferably 100% of the A groups are a) homopolymers of oxyalkylene having no more than 15 units, preferably no more than 10 units, more preferably no more than 7 units, most preferably no more than 4 units or b) block copolymers of oxyalkylenes having homopolymeric subblocks no more than 15 units, preferably no more than 10 units, more preferably no more than 7 units, most preferably no more than 4 units per subblock or c) mixtures of a) and b). Each oxyalkylene unit is selected from

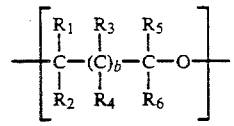

(Ia)

in which b is zero to 4, from each of $R_1$, $R_2$, $R_5$, and $R_6$, are independently selected from the group H, aliphatic, aromatic or heterocyclic containing radical such as: unsubstituted $C_1$–$C_{16}$ alkyl; substituted $C_1$–$C_{16}$ alkyl; unsubstituted $C_2$–$C_{16}$ alkenyl; and substituted $C_2$–$C_{16}$ alkenyl; wherein the alkyl and alkenyl substituents are independently selected from $C_1$–$C_{16}$ alkoxycarbonyl, $C_2$–$C_{16}$ alkenyloxycarbonyl, fluoro, aryl of up to 10 carbon atoms, $C_1$–$C_8$ alkoxy, $C_2$–$C_6$ alkanoyloxy, aryloxy of up to 10 carbon atoms, $C_3$–$C_6$ alkenoyloxy, aroyloxy of up to 11 carbon atoms, $C_3$–$C_8$ cycloalkyl, $C_3$–$C_8$ cycloalkyloxy, $C_3$–$C_8$ cycloalkyl-carbonyloxy, $C_3$–$C_8$ cycloalkoxy-carbonyl, oxacycloalkyl of up to 7 carbon atoms, oxacycloalkoxy of up to 7 carbon atoms, oxacycloalkoxy (up to 7 carbon atoms)-carbonyl, oxacycloalkyl (up to 7 carbon atoms)-carbonyloxy, and aryl (of up to 10 carbon atoms)-oxycarbonyl, each of said alkyl and alkenyl substituents being, in turn, optionally substituted by $C_1$–$C_6$ alkyl, fluoro or a $C_1$–$C_6$ alkoxy provided said last mentioned alkoxy is not bound to a carbon atom already bound to another oxygen atom; $R_1$, $R_2$, $R_5$, and $R_6$ being further independently selected from aryl of up to 10 carbon atoms, $C_3$–$C_8$ cycloalkyl, and oxacycloalkyl of up to 7 carbon atoms, each of which may be unsubstituted or further substituted with a substituent selected from the group of substituents for said alkyl set forth above; each $R_3$ and $R_4$ are selected from the same group set forth above for $R_1$; and $R_3$ and $R_4$ are further independently selected from $C_1$-$C_{16}$ alkoxycarbonyl, $C_2$-$C_{16}$ alkanoyloxy, $C_2$-$C_{16}$ alkenoxycarbonyl, and $C_3$-$C_{16}$ alkenoyloxy, each of which may be further substituted by fluoro, aryl of up to 10 carbon atoms, or $C_1$-$C_{16}$ alkoxy, and $R_3$ and $R_4$ are still further independently selected from aryloxy of up to 10 carbon atoms, cycloalkoxy of up to 8 carbon atoms, cycloalkyl (of up to 8 carbon atoms)-carbonyloxy, cycloalkoxy (of up to 8 carbon atoms)-carbonyl, aroyloxy of up to 11 carbon atoms, oxacycloalkoxy of up to 7 carbon atoms, oxacycloalkenoxy of up to 7 carbon atoms, oxacycloalkoxy (of up to 7 carbon atoms)-carbonyl, oxacycloalkyl (of up to 7 carbon atoms)-carbonyloxy, oxacycloalkenyloxy (of up to 7 carbon atoms)-carbonyl and aryloxy (of up to 10 carbon atoms)-carbonyl, each of which may be further substituted by fluoro, $C_1$-$C_6$ alkyl or $C_1$-$C_6$ alkoxy, provided that any substituent having an oxygen atom or carbonyl group thereof as its link to the rest of the molecule may not be a substituent on the same carbon atom which is bonded to another oxygen atom. In addition, 2 adjacent groups selected from $R_1$ to $R_6$, together with the atoms to which they are attached, may form a 5-8 membered cycloalkyl, oxacycloalkyl or bicycloalkyl ring. When each b is 0, at least one of $R_1$, $R_2$, $R_5$ and $R_6$ in at least a portion of the segments having formula I is other than hydrogen. The polymer is sufficiently hydrophilic that it exhibits a receding contact angle with distilled water at 20° C. of less than 60°, preferably less than 40°, more preferably less than 25°, even more preferably less than 15°, most preferably less than 10°.

In the foregoing, all alkyl groups whether mentioned alone or as part of another group are preferably $C_1$-$C_4$ alkyl, such as methyl, ethyl, propyl and butyl, especially t-butyl, with the exception that adjacent groups on aryl rings cannot each be t-butyl. These alkyl groups may be straight chain or branched chain. When the alkyl is a substituent on a phenyl ring, it is preferably attached at the para position. Preferably alkenyl groups, whether alone or as part of another group are $C_2$-$C_4$ alkenyl, such as ethenyl, propenyl, or butenyl. Preferred aryl groups (whether alone or as part of another group) are phenyl or naphthyl, more preferably phenyl. Preferably, the aryl groups are still further substituted by $C_1$-$C_4$ alkyl, more preferably t-butyl, most preferably in the para position.

Each A group can have from 1 to 1000 oxyalkylene units, preferably 1-200, more preferably 1-150 units, still more preferably 1-100 units, yet more preferably 1-75 units, most preferably 1-50 units.

At least 30% of the A groups are independently selected from polyoxyalkylene groups selected from a) homopolymer blocks of the formula J

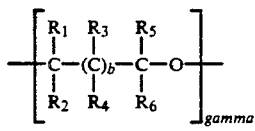 (J)

wherein b is 0 to 4, gamma and $R_1$-$R_6$ are as defined below; and b) copolymer blocks of the formula B

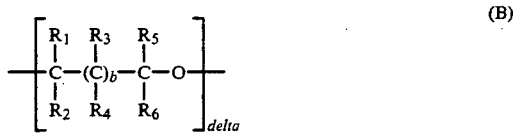 (B)

wherein b is 0 to 4, and delta and $R_1$-$R_6$ are as defined below; wherein gamma is up to 15 and delta is up to 1000 provided that within delta, there is no homopolymeric block of more than 15 oxyalkylene units, the remaining groups being homopolymers or copolymers of the formula C

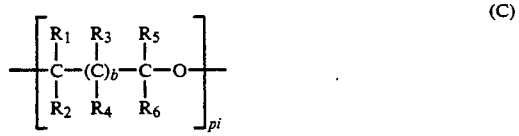 (C)

wherein pi is up to 1000 repeating units without regard for the size of the homopolymeric sub-blocks within pi; the terminal oxygen within an A group being replaced by —O— or —$NR_7$—.

Two most preferably embodiments are when at least 30% of the A groups in the polymer consist of 32% and 35% polyethylene glycol and 68% and 65%, respectively of polypropylene glycol, the polyethylene glycol blocks being of no more than three repeating units each and the polypropylene glycol blocks being of no more than seven repeating units each.

each w is 1-8;
each D is —O— or —$NR_7$— in which
$R_7$ is H, lower alkyl, or phenyl;
each L is independently selected from —BRB-'B—R— or R—B' wherein
each B and B' is independently selected from

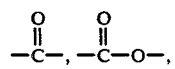

and

with the carbonyl group thereof being bound to A or D;

each R is a divalent linking group preferably selected from i) a divalent aliphatic group, preferably alkyl, alkenyl, or alkynyl, of up to 25 carbon atoms which may be interrupted by an interrupting unit selected from oxy, carbonyloxy, amino, aminocarbonyl, oxycarbonyl, ureido, oxycarbonylamino, and carbonylamino;

ii) a divalent -(aliphatic)$_{alpha}$- 5-7 membered cycloaliphatic -(aliphatic)$_{beta}$- wherein each of alpha and beta are independently 0 or 1, and each of the non cyclic aliphatic groups are independently selected from group i) above, preferably said group ii) has up to 25 carbon atoms;

iii) a divalent-(aliphatyl)$_{alpha}$-aryl-(aliphatyl)$_{beta}$- having 6 to 25, preferably 7-16 carbon atoms in the aryl portions; and each of the aliphatic groups are independently selected from group i) above and alpha and beta are independently 0 or 1, wherein groups ii) and iii) can be interrupted in the non-cyclic portions thereof or between the cyclic and non-cyclic portions thereof by an interrupting group of part i), and groups iii) may be further substituted with one or more substituents selected from halogen, preferably fluorine or chlorine, $C_{1-4}$ alkyl, preferably methyl, and $C_{1-12}$ perhaloalkyl, especially $C_{1-12}$ perfluoroalkyl.

Preferably each b is independently 0-3, most preferably 1-2. A further preferred embodiment is that the group identified by formula I be at least 25% halogen free, preferably 30%, still more preferably 40%, even more preferably substantially halogen free and most preferably, totally halogen free. Wherever cyclo groups are indicated, whether carbocyclic or heterocyclic they preferably have 5-6 ring members and the heterocyclics preferably have only carbon and an oxygen atom as a ring member.

In formula Ia, when b is greater than one, each of the multiple $R_3$ and $R_4$ groups may be the same or different; however preferably all of the $R_3$ groups are the same and all of the $R_4$ groups are the same.

Preferably, each b is independently an integer of 0 to 2, and most preferably zero or one.

In one particularly preferred aspect of the invention, each of $R_1$-$R_5$ is hydrogen, and if each b within an A group is zero, then at least a portion of the $R_6$ groups are methyl.

Preferred substituents for $R_6$ are alkyl of up to 16 carbon atoms; alkyl of up to 16 carbon atoms substituted by alkoxy of up to 8 carbon atoms, or fluoro; phenyl which is unsubstituted or substituted by fluoro, alkoxy of up to 6 carbon atoms or alkyl of up to 6 carbon atoms; benzyl, wherein the phenyl ring thereof is unsubstituted or substituted by fluoro, alkoxy of up to 6 carbon atoms or alkyl of up to 6 carbon atoms cyclohexyl; or oxacycloalkyl of 4 to 5 ring carbon atoms.

A highly advantageous subembodiment relates to wettable ophthalmic devices, preferably contact lenses, fabricated from a polymer containing segments of the formula

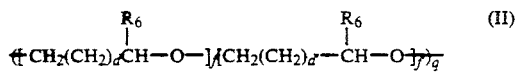

wherein each d and d' is selected from the same group as b in formula Ia and that each f and f' within formula II cannot exceed 15.

Preferably, at least one $R_6$ within each formula II is an aliphatic, aromatic, or heterocyclic radical, preferably alkyl of up to 6 carbon atoms; alkyl of up to 6 carbon atoms substituted by alkoxy of up to 6 carbon atoms or fluoro; phenyl which is unsubstituted or substituted by fluoro, alkoxy of up to 6 carbon atoms or alkyl of up to 6 carbon atoms; benzyl wherein the phenyl ring thereof is unsubstituted or substituted by fluoro, alkoxy of up to 6 carbon atoms or alkyl of up to 6 carbon atoms; cyclohexyl or oxacycloalkyl of 4 to 5 ring carbon atoms.

Free hydroxy groups on the outer surfaces of the formed polymer are more preferable than in the interior of the polymer in that they increase wettability without drawing water into the polymer maxtrix. A suitable means of tying up excess free hydroxy groups present would be to interact them with a color group. Typical color groups useful in these embodiments include, but are not limited to the hydroxy-reactive dyes known in the art under the tradename Remazol, manufactured by American Hoechst. Examples of the Remazol dyes which are especially suitable are:

Remazol Brill Blue RW (Color Index Code: Reactive Blue 19);
Remazol Yellow GR (Color Index Code: Reactive Yellow 15);
Remazol Black B (Color Index Code: Reactive Black 5);
Remazol Golden Orange 3GA (Color Index Code: Reactive Orange 78); and
Remazol Turquoise P (Color Index Code: Reactive Blue 21);
all of which have at least one group of the formula

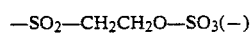

which reacts with the polymer or monomer hydroxy group to yield a

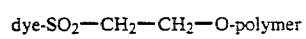

or

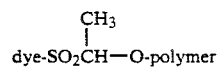

group, preferably the former. In such a manner, both excess free hydroxy groups are disposed of and colored contact lenses can be realized simultaneously. Another means of disposing of these excessive hydroxy groups is to utilize their presence to form various degrees and types of crosslinking.

In a further embodiment of the invention, the ophthalmic device, preferably a contact lens, is fabricated from a polymer consisting essentially of polymerized units of a reactive monomer of the formula $$L'-D-[A-L-D]_w-A-L'' \qquad (III)$$

wherein
each A is independently a divalent moiety of formula Ia, provided that not all A groups in any one polymer can be homopolymers of polyethylene glycol, preferable all A groups cannot be homopolymers of polyethylene glycol or polypropylene glycol, and provided that the terminal oxygen atom within any one or more A groups may be replaced by

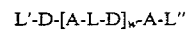

each L is independently selected from —BRB'—; w is 0-8, preferably 0-4, most preferably 0, 1 or 2; D is oxygen or —N($R_7$)—; each $R_7$ is independently selected from H, $C_1$-$C_4$ alkyl, phenyl, preferably H; each B and B' being selected from

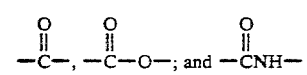

with the carbonyl group being bound to A or D; each R is a divalent linking group preferably selected from
i) a divalent aliphatic group preferably alkyl, alkenyl, of up to 25 carbon atoms which may be interrupted by oxy, carbonyloxy, amino, aminocarbonyl, oxycarbonyl, ureido, oxycarbonylamino, or carbonylamino;

ii) a divalent 5-7 membered cycloaliphatic having 5-25 carbon atoms;

iii) a divalent arylene group having 6-25, preferably 7-15 carbon atoms; and iv) a divalent aralkyl or alkaryl having 7 to 25 preferably 8-16 carbon atoms; wherein groups ii) and iv) can be optionally interrupted by the same groups as in group i) and wherein the aryl rings in groups iii) and iv) may be further substituted with one or more substituents selected from halogen, preferably fluorine or chlorine, $C_1$-$C_4$ alkyl, preferably methyl, and $C_1$-$C_{12}$ perhalo alkyl, especially $C_1$-$C_{12}$ perfluoro alkyl;

L' is selected from H, P'-B-R-B'-, and P'-R-B'- wherein B, R, and B' are as defined above with the carbonyl group of B being bound to P', and P' is H, $NH_2$, OH, or a moiety containing a crosslinkable group which may be crosslinked when coreacted with a suitable crosslinking agent or when irradiated by actinic radiation; and L" is selected from H; L''' as defined hereinafter, -B-R-B'-P', and B-R-P', wherein B, R, B' and P' are as defined above except that the carbonyl of B' instead of B is bound to P'; and L''' is a terminal monovalent aliphatic, aromatic, or cycloaliphatic group of up to 14 carbon atoms.

When P' is a vinyl containing group, for example $$\begin{array}{c} HC=C-\\ | \quad |\\ R_b \quad R_a \end{array}$$

with $R_a$ and $R_b$ as defined below,
then the monomer of formula III can be crosslinked in the presence or absence of up to about 10% of other vinylic comonomers, provided that such comonomers are substantially free of hydroxy groups in the final product.

The vinylic comonomer is frequently utilized to increase the hydrophilicity of the final product without substantially altering the other properties mentioned above. Typically, when the vinylic comonomer is a polyethylene glycol of the formula $$R_9-\overset{O}{\underset{\|}{C}}-O-(CH_2CH_2O)_n-R_8$$

or pyrrolidone of the formula $$R_9-N\underset{\diagdown\quad\diagup}{\diagup\quad\diagdown}=O$$

with n being 1-25, $R_8$ being H or $CH_3$ and $R_9$ being $CH_2=CH-$, $CH_2=CH-$, $CH_2-C(CH_3)-$ or other UV curable moiety, the resultant polymer is more hydrophillic than previously, but the Dk is essentially the same as when the comonomer is absent.

Usually, when present, the vinylic comonomer is used in an amount of about 2% to about 10% by weight of the resultant polymer. Advantageously, no more than 5% of vinylic comonomer is used when the compound of formula III has a molecular weight in excess of 8000. Generally, when the compound of formula III has a molecular weight of under about 4000, up to 10% by weight of vinylic comonomer can be used. When the compound of formula III has a molecular weight between 4,000 and 8,000, the maximum amount of vinylic comonomer is between 5% and 10% by weight.

When P' does not have a vinylic group, but takes part in crosslinking, P' contains an active hydrogen. Preferably P' terminates in a OH, $NHR_c$ ($R_c$ being H or lower alkyl), a leaving group bound directly to the B or B' carbonyl, a conventional acyl leaving group when not so bound, SCN— or OCN—. Crosslinking is then typically carried out by condensation or addition with a di or polyfunctional coreactive monomer. For example, when P' is OH, then the coreactive monomer functional group can be —$NHR_c$, —COOH, OCN, SCN, etc.; when P' is $NHR_c$, the reactive comonomer functional group can be a conventional acyl, or acyl bound to a conventional leaving group; and when P' has OCN— or SCN—, then the reactive comonomer functional group can be OH. Similarly, the other coreactive functional groups mentioned in terms of either P' or the coreactive monomer can be interchanged. Those mentioned as part of P' being on the coreactive monomer and those mentioned as part of the coreactive monomer being part of P'.

Suitable vinylic monomers and coreactive monomers for condensation are set forth below. However, the list is not exhaustive and those of ordinary skill will appreciate the modifications, additions, and alternatives which may also be employed.

Minor amounts i.e. less than 50%, preferably up to 30%, and most preferably up to no more than about 10% by weight, of conventional copolymerizible vinyl monomers can be employed as extenders or hydrophilic modifiers, or the like, in the preparation of the instant polymer, as copolymer constituents. Suitable vinyl monomers include:

acylates and methacrylates of the general formula $$\begin{array}{c} R_{16}\\ |\\ H_2C=C-COOR_{17} \end{array}$$

where $R_{16}$ is hydrogen or methyl and $R_{17}$ is a straight chain or branched aliphatic, cycloaliphatic or aromatic group having up to 20 carbon atoms which is unsubstituted or substituted by one or more alkoxy, alkanoyloxy or alkyl of up to 12 carbon atoms, or by halo, especially chloro or preferably fluoro, or $C_3$-$C_5$ polyalkyleneoxy of 2 to about 100 units;

acrylamides and methacrylamides of the general formula $$\begin{array}{c} H_2C=C-CONHR_{17}\\ |\\ R_{16} \end{array}$$

where $R_{16}$ and $R_{17}$ are defined above; vinyl ethers of the formula $$H_2C=CH-O-R_{17}$$

where $R_{17}$ is as defined above; vinyl esters of the formula $$H_2C=CH-OOC-R_{17}$$

where $R_{17}$ is as defined above; maleates and fumarates of the formula $$R_{17}OOC-HC=CH-COOR_{17}$$

where $R_{17}$ is as defined above; and vinylic substituted hydrocarbons of the formula $$R_{16}CH=CHR_{17} \qquad 5$$

where $R_{16}$ and $R_{17}$ are as defined above.

Useful monomers include, for example:

methyl-, ethyl-, propyl-, isopropyl-, butyl-, ethoxyethyl-, methoxyethyl-, ethoxypropyl-, phenyl-, benzyl-, cyclohexyl-, hexafluoroisopropyl-, or n-octyl-acrylates and -methacrylates as well as the corresponding acrylamides and methacrylamides;

dimethylfumarate, dimethylmaleate, diethylfumarate, methyl vinyl ether, ethoxyethyl vinyl ether, vinyl acetate, vinyl propionate, vinyl benzoate, acrylonitrile, styrene, alphamethyl styrene, 1-hexene, vinyl chloride, vinyl methyl ketone, vinyl stearate, 2-hexene and 2-ethylhexyl methacrylate.

As hydrophilic modifiers, to increase hydrophilicity without substantial loss of DK, the vinyl comonomer can be a N-(vinyl containing group)-pyrrolidone or a polyoxyethylene (of 1-25 repeating units) acrylate or methacrylate, or other hydrophilic modifier as defined by the copending U.S. Pat. Nos. 4,859,780 and 4,921,956.

P' with P' being H, at least one additional crosslinkable moiety must be present as one of, or a substituent on one of the groups $R_1$-$R_6$. Such crosslinkable groups may also be present as a substituent on or in place of one or more of $R_1$-$R_6$ even when both L' and L'' have crosslinkable groups therein. However, the degree of crosslinking in the finished crosslinked polymer should not exceed 10%, preferably not greater than 5%, more preferably be in the range of 1-4%, most preferably in the range of 2-3%.

In a preferred embodiment, A is the divalent moiety according to formula II.

Especially preferred are polymers of the monomer according to formula III in which L' and/or L'' is

wherein $R_a$ and $R_b$ are each independently H or $CH_3$, but not simultaneously $CH_3$.

A valuable sub-embodiment of the invention relates to ophthalmic devices, preferably contact lenses, of polymers consisting essentially of polymerized units of the formula

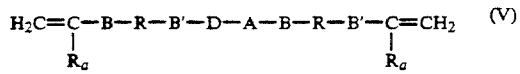

wherein $R_a$, B, R, B' and A are as defined above, each $R_a$ being independent of the other. Particularly preferred are polymers of the monomers of formula IV and V wherein R is a divalent arylene group of 6 to 14 carbon atoms, or is a divalent $C_2$-$C_6$ alkylene-oxycarbonyl-$C_6$-$C_{10}$-arylene group; D is —O—; and B and B' are each —NHCO— wherein the nitrogens thereof are directly bonded to R.

Also highly preferred are those polymers of monomers of formula III and V wherein A is of the formula

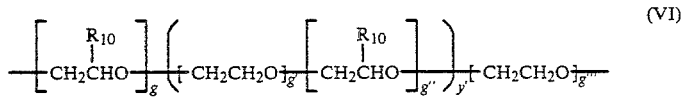

wherein one of g and g''' is zero and the other and g' and g'' are independently 1-20, y' is a number such that $g+g'''+g'y+g''y=4-1000$. Another valuable embodiment requires the value of g'' to be at least about twice that of g' and $R_{10}$ to be alkyl of 1 to 4 carbon atoms, preferably methyl.

The above reactive vinylic monomers are characteristically polymerized under conventional polymerization conditions. In those vinylic monomers containing but one vinyl group, a minor amount e.g. from about 0.01 to about 5 weight percent, based on the monomer of formula III, of a conventional crosslinking agent, may be employed. Suitable crosslinking agents include diolefinic monomers such as:

Allyl acrylate and methacrylate; alkylene glycol and polyalkylene glycol di-acrylates and -methacrylates, such as ethyleneglycol dimethacrylate, diethylene glycol dimethacrylate, and propylene glycol dimethacrylate; trimethylol propane triacrylate; pentaerythritol tetracrylate, divinylbenzene; divinyl ether; divinyl sulfone;

bisphenol A diacrylate or methacrylate; methylene bisacrylamide; diallyl phthalate; triallyl melamine and hexamethylene di-acrylate and -methacrylate. Also, such minor amounts of a crosslinking agent may be employed, if desired, in the polymerization of the divinyl monomer of formula III and V.

When the monomers of formula III have free hydroxy, isocyanato, carboxylic acid, or amine groups, suitable crosslinking agents contain di or poly functional co-reactive groups to form addition or condensation reactions linking 2 or more chains.

If desired, the monomer reaction mixture may contain a catalytic amount of a conventional catalyst, preferably a free radical catalyst. Of particular interest are conventional peroxide and azo catalysts, such as hydrogen peroxide, benzoyl peroxide, tert-butyl peroctoate, benzoyl perodixe or azobis(isobutyrylnitrile).

The polymerization can generally be carried out at temperatures between about 20° to about 150° C., for a period between about 1 to about 24 hours. It is understood that the time and temperature in such a reaction are inversely related. Thus, temperatures employed in the upper end of the temperature range will generally provide reaction times near the lower end of the time range. Preferably, the polymerization is conducted in the presence of actinic radiation, such as UV light.

Depending upon the nature of the polymer mixture, it may be desirable for the polymers obtained from such polymerizations to be post cured, e.g. at a somewhat elevated temperature such as between about 60° C. to about 150° C.

For the preparation of contact lenses, the polymer mixture may be cast directly in the shape of the lens, or the polymerization may be carried out in a mold having a shape convenient for further processing, such as in the shape of small cylinders or "buttons", which can then be machined.

In yet a further subembodiment of the invention, the ophthalmic device, preferably a contact lens, is fabricated from a polymer consisting essentially of an addition product of $$E-Y_1-D-(A-L-D)_w-A-Y_1-E \qquad (VII)$$

and $$(E^1)_t-G \qquad (VIII)$$

wherein A, L, D and w are as defined above;

t is an integer of 2 to 4;

G is an aliphatic, aromatic, araliphatic, carbocyclic or heterocyclic residue having a valency corresponding to the value of t and containing up to about 24 carbon atoms, or where t is 2, may also represent a divalent group of the formula $$-Y_1-D-(A-L-D)_w-A-Y_1-;$$

$Y_1$ is a divalent aliphatic group of up to 14 carbon atoms which may be interrupted by oxy, carbonyloxy, amino, aminocarbonyl, oxycarbonyl, ureido, oxycarbonylamino or carbonyl; a divalent aliphatic hydrocarbonyl - carbonyl or - aminocarbonyl group of up to 14 carbon atoms and wherein the carbonyl group thereof is covalently bonded to the adjacent oxygen or NR7 moiety; a divalent 5 to 7-membered cycloaliphatic group of from 5 to 14 carbon atoms; a divalent arylene group of 6 to 14 carbon atoms; a divalent aralkyl or alkaryl group of 7 to 14 carbon atoms; a divalent 5 to 7-membered cycloaliphatic - carbonyl or - aminocarbonyl group of from 6 to 15 carbon atoms, wherein the carbonyl groups thereof is covalently bonded to the adjacent oxygen or NR7 moiety; or a divalent arylene -, aralkyl - or alkaryl - carbonyl or -aminocarbonyl group wherein the arylene group is of 6 to 14 carbon atoms, the aralkyl or alkaryl group is of 7 to 14 carbon atoms, and the carbonyl group is covalently bonded to the adjacent oxygen or NR7 moiety; or $Y_1$ is a direct bond where E is hydrogen;

E is hydrogen, hydroxy or amino when $E^1$ is isocyanato or isothiocyanato; and E is isocyanato or isothiocyanato when $E^1$ is hydroxy or amino.

Advantageously, in order to insure adequate crosslinking, in one subembodiment there is employed at least a minor amount of those compounds wherein t is 3, for example at about 0.2% by weight based upon the amount of compound of formula IV employed. Generally, a stoichiometrically equivalent amount of the compounds of VII and VIII are combined; however a slight excess of di- or polyisocyanate or isothiocyanate may be employed to insure sufficient crosslinking to maintain dimensional stability in the product. As a further alternative, additional conventional crosslinking agents may be employed to insure sufficient crosslinking such that the product maintains dimensional stability. Thus, in addition to the compounds of formula VII and VIII, there may also be added to the reaction mixture a minor amount, e.g. up to about 5 weight percent, of a conventional di-isocyanate or tri-isocyanate such a toluene di-isocyanate, isophorone di-isocyanate, 4,4'-methylenebis(phenyl isocyanate), methylenebis(cyclohexyl isocyanate), melamine tri-isocyanate, and the like. Alternatively where a stoichiometric excess of isocyanate is employed in the reaction of VII and VIII, a minor amount, e.g. up to about 5 weight percent, of a di- or polyfunctional amine or hydroxylated crosslinking agent may be employed. Suitable such crosslinking agents include, for example ethylene glycol, glycerin, diethylene glycol, ethylene diamine, ethanolamine, triethanolamine, diethanolamine and the like.

The addition reaction between the compounds of formula VII and formula VIII and any additional crosslinker can be conducted under conditions known, per se. Thus, the compounds may be simply admixed, in the presence of an inert diluent if necessary or desired, at a reaction temperature between about 0° C. and about 100° C., preferably between about 20° C. and 80° C., optionally in the presence of a condensation catalyst, such as triethyl amine or di-n-butyltin diacetate.

In the preparation of ophthalmi devices, such as contact lenses, the reaction mixture may be cast directly in the shape of the lens, or the polymerization may be carried out in a mold having a shape convenient for further processing, such as the shape of a small cylinder or "button", which can then be machined.

The compounds of the formula III, V, VII, and VIII are either known or can be prepared by methods which are known, per se.

For example, the vinylic monomers of formula V can be prepared by reacting either (a) a mono-ol of the formula $$HO-(A-L-D)_w-A-L''' \qquad (IX)$$

where L''' is a terminal monovalent aliphatic, aromatic or cycloaliphatic group of up to 14 carbon atoms, or (b) a diol of the formula $$HO-(A-L-D)_w-A-H \qquad (X)$$

wherein A, L, D and w are as defined above, with a stoichiometric amount of a vinylic compound of the formula $$H_2C=C-BR-X \qquad (XI)$$
$$\underset{R_a}{|}$$

wherein X is a isocyanato group; an activated carboxy group, such as an anhydride, an acid halide, or a carboxy ester; or is a leaving group, such as a halide, sulfato, or the like, at temperatures between about 0° C. to about 100° C., in the presence or absence of a conventional additional catalyst, and in the optional presence of an inert diluent, and recovering the product of formula V. Where X is a leaving group, such as a halide, the product of formula (X) may be in the form of its alkoxide, such as alkali metal alkoxide, salt.

Alternatively, one may prepare products of formula III wherein B and B' are —NHCO— and D is —O— by reacting a diisocyanate, such as an aliphatic, aromatic, cycloaliphatic, or araliphatic diisocyanate with a monool or diol according to formula IX or X, respectively, and react the corresponding isocyanato terminated product with a hydroxy containing acrylate or methacylate, such as hydroxyethyl-acrylate or -methacrylate, or an allyl amine or methallyl amine or allyl or methallyl alcohol to form the corresponding product of formula III at a temperature between about 0° C. and 100° C., in the presence or absence of an inert diluent, and optionally in the presence of an addition catalyst, such as a tertiary amine, e.g. triethylamine or an organo-tin compound and recovering the product of formula III.

Still further, compounds of formula XII can be reacted with compounds of the formula $$X-R-X \qquad (XII)$$

where R and X are as defined above, to form a compound of the formula $$X-R-B-(A-L-D)_w-A-B-R-X \qquad (XIII).$$

Compounds of formula XIII are then reacted with an X coreactive moiety which also contains a vinyl group, for example hydroxy ethyl methacrylate to yield a compound of formula III.

The compounds of formula IX and formula X are known or can easily be prepared by methods known per se.

For example, the compounds of formula X can be prepared by reacting a diol of the formula HO—A—H with a difunctional reactive group containing compound having the group L wherein the reactive groups are isocyanate, activated carboxy, such as an anhydride, an acid halide or a carboxy ester, or is a leaving groups, such as halide, sulfato or the like. Where the molar ratio of diol to the difunctional reactive group containing compound is about 2 to 1, the value of w in the resulting adduct of formula (X) is about 1; where about 3 moles of diol are reacted with about 2 moles of the difunctional group containing compound, the resulting average value of w in the adduct of formula (X) is characteristically about 2, and so on. The aforementioned reaction to obtain those compounds of formula (X) where w is 1 or greater, can be conducted at a reaction temperature between about $-10°$ C. to about $100°$ C. depending on the relative reactivities of the species involved, in the presence or absence of an inert diluent and in the optional presence of an addition catalyst, if desired or appropriate.

Suitable polyols and amino polyethers of the formula HD-A-H wherein A represents the divalent moiety of formula I are generally known materials or can be prepared by methods known, per se.

Thus, the polyols of the formula HO-A-H are generally prepared by the addition reaction of an epoxide of the formula

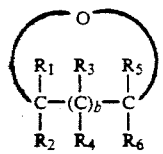

where $R_1$–$R_6$, and b, are as defined above, with another epoxide of formula (XIV) optionally in the presence of a conventional alkylation catalyst, at atmospheric to elevated pressures of up to about 30 atmospheres gauge, at temperatures between $0°$ C. to about $130°$ C., optionally in the presence of an inert diluent. If desired, one may add to the reaction mixture, prior to the reaction of the epoxides, an aliphatic, aromatic or cycloaliphatic alcohol, acid or amine having up to 14 carbon atoms to prepare the corresponding mono-ols terminating in the group D.

The reaction between the epoxides, when mixtures of different epoxides are employed to obtain the polyol of the formula HO—A—H, can be conducted by admixing the epoxides to obtain random copolymers or terpolymers, etc., or the addition can be conducted sequentially to form block copolymers having terminal hydroxy groups. Suitable catalysts include alkaline earth oxides, alkaline earth carbonates, alkyl zinc compounds, aluminum alkoxides, hydrates of ferric chloride, bromide and acetate, and gamma radiation. The reaction may also by initiated by the presence of a glycol, such as ethylene glycol or propylene glycol or by a polyol of higher functionality such as sucrose, or by an amine, such as ethylene diamine, toluenediamine, and so forth. Generally the length of time of the reaction will depend in part on the alkylene oxide employed, but can generally be from less than one to several score hours. Thus, ethylene oxide generally is about three times as active as propylene oxide, which in turn reacts more rapidly than 1,2-butylene oxide. The preparation of polyoxitanes and polytetrahydrofurans are generally initiated via ring opening oxonium formation using trialkyloxonium salts, carboxonium salts, acylium salts and the like.

Suitable diols of the formula HO—A—H include those prepared from epoxides such as:

1,2-propylene oxide; 1,2-butylene oxide; 1,2-epoxydecane; 1,2-epoxydodecane; 1,2-epoxyoctane; 2,3-epoxynorbornane; 1,2-epoxy-3-ethoxypropane; 1,2-epoxy-3-phenoxypropane; 2,3-epoxypropyl 4-methoxyphenyl ether; tetrahydrofuran; 1,2-epoxy-3-cyclohexyloxypropane; oxetane; 1,2-epoxy-5-hexene; 1,2-epoxyethylbenzene; 1,2-epoxy-1 methoxy-2-methylpropane; perfluorohexylethoxypropylene oxide; benzyloxypropylene oxide; and the like. Also, the aforementioned epoxides may be employed as mixtures thereof. Further, certain cyclic ethers of formula XIV, where b is 3 and the carbocyclic portion of the ring is substituted are resistant to polymerization alone, but copolymerize quite readily with more reactive cyclic ethers. Suitable co-monomers include, for example, 2-methyl-tetrahydrofuran and 3-methyl-tetrahydrofuran. Also, while ethylene oxide may be employed as a co-monomer, ethylene oxide polymers, in the absence of more hydrophobic units, is characteristically too hydrophilic and too excessively absorbs aqueous fluid to be of use in accordance with the instant invention. However, ethylene oxide/propylene oxide copolymeric diols wherein there is greater than 60% propylene oxide, on a mole basis, is sufficiently hydrophobic so as to be substantially non-swellable in aqueous media, and yet sufficiently hydrophilic so as to exhibit a contact anglo with water of less than $60°$; preferably less than $40°$, more preferably less than $25°$, more preferably less than $15°$, most preferably less than $10°$.

In general, the amount of ethoxy units in the polymer backbone of the instant polymeric ophthalmic devices will depend upon the amount of water absorbed by such polymer under use conditions. The polymers for use according to the instant invention characteristically absorb more than about 10% by weight water based upon the total weight of polymer, preferably not more than about 90% by weight water, more preferably 20%–75%, still more preferably 35–55% by weight water. The absorption amount of water is generally or conveniently measured at about $20°$ C. using distilled water or, if desired, an isotonic solution.

Many polymer diols of the formula HO—A—H which can be used in minor amounts are commercially available, and include poloxamers having the general formula

wherein b' has a value between about 16 and 70 and the sum of a' and c' is between about 4 to about 100. Examples of such poloxamers, and their average values of a', b' and c', include poloxamer 101 (a' is 2, b' is 16, c' is 2); polyoxamer 105 (a' is 11, b' is 16, c' is 11); poloxamer 108 (a' is 46, b' is 16, c' is 46); poloxamer 122 (a' is 5, b' is 21, c' is 5); poloxamer 124 (a' is 11, b' is 21, c' is 11); poloxamer 181 (a' is 3, b' is 30, c' is 3); poloxamer 182 (a' is 8, b' is 30, c' is 8); poloxamer 183 (a' is 10, b' is 30, c' is 10); poloxamer 185 (a' is 19, b' is 30, c' is 19); poloxamer 212 (a' is 8, b' is 35, c' is 8); poloxamer 231 (a' is 6, b' is 39, c' is 6); poloxamer 282 (a' is 10, b' is 47, c' is 10); poloxamer 331 (a' is 7, b' is 54, c' is 7); poloxamer 401 (a' is 6, b' is 67, c' is 6).

Such polyoxamers are available, e.g. from BASF Wyandotte under their Pluronic ® brand name.

Polypropylene ether glycols include commercially available products having a molecular weight range between about 400 to about 4,000. Also commercially available are polytetramethylene ether glycols of moderately low molecular weight, generally between about 1,000 and 2,000, and polymers of 1,2 butylene oxide, i.e. polybutyl ether glycol.

As stated above, the polymers for use in the instant invention are those which exhibit a receding contact angle at 20° C. of less than 60°, preferably less than 40°, more preferably less than 25°, more preferably less than 15° and most preferably less than 10°. The measurement of such contact angle is conveniently performed using a modified "Wilhelmy Plate" technique, as described, for example, for J. D. Androde, et al. *Surface and Interfacial Aspects of Biomedical Polymers*, Vol. 1, *Surface Chemistry and Physics*, Plenum Press, 1985, wherein a specimen sample in the form of a plate of known dimensions is immersed into the wetting solution, pure water, at a slow controlled rate, e.g. at 2-20 mm per minute. Poly(hydroxyethylmethacrylate) generally has, under these conditions, a receding contact angle of 39°-43°.

As mentioned above, the instant polymers for use in the present invention possess a high degree of oxygen permeability. The oxygen permeability, $Dk(\times 10^{-10})$, is measured using a modification of ASTM standard D3985-81 in that (a) there is used 21% oxygen, i.e. air, instead of 99-100% oxygen, (b) the surface area of sample employed is 0.50 square meters versus 100 square meters and the humidity is controlled to be at 95-100% relative humidity instead of 0% relative humidity. The unit of Dk is (cm.mm/s) (ml $O_2$/ml.mmHg).

Typically, conventional fully swollen polyhydroxyethyl methacrylate lenses which are sparingly crosslinked possess a $Dk(\times 10^{-10})$ (cm.mm/s) (ml $O_2$/ml.mmHg) value of about 5-7.

The oxygen permeability of the instant polymers for use as an ophthalmic device, such as a contact lens, advantageously possess a $Dk(\times 10^{-10})$ value generally greater than 7, preferably greater than about 15, more preferably greater than about 20 and most preferably greater than about 40.

The following examples are for illustrative purposes and are not to be construed as limiting the invention. All parts are by weight unless otherwise specified.

All of the following Examples have procedures common to each. These common procedures are as follows:

1. All glassware is dried in an oven which is at 150° C. for at least 5-6 hours.
2. When assembled the reaction system must stay under a constant nitrogen environment.
3. All of the isocyanates used should be freshly distilled.
4. All of the polyglycol material should contain no more than 0.005% water. For these Examples all of the diols were stripped of water using a Pope wipe film still at 65° C. and less than 2 mm mercury.
5. After the reaction glassware is assembled and under a Nitrogen atmosphere the set up is flame dried for 20 minutes to ensure that all of the moisture is absent from the system.
6. All of the methylene chloride used in these reactions is distilled into molecular seives thru a 20 mm column packed with glass helices.

EXAMPLE 1

1.0 mole of propylene glycol (previously dried using 4A molecular sieves) and 3% by weight KOH are added to a stainless steel reactor, purged with nitrogen 5-7 times and then evacuated to 0 psig for at least 20-30 minutes. During this time period, the reaction mixture is gradually heated to 100° C. The reaction mixture vacuum is broken with a nitrogen sparge to approximately 1-2 psig. Then 4 mole of ethylene oxide is added in a manner so as not to exceed a temperature of 180° C. and a pressure of 80 psig. The ethylene oxide is reacted down to 3-4 psig. 11.5 mole of propylene oxide is then added to the reaction mixture in such a manner as not to exceed a temperature of 180° C. and a pressure of 80 psig, which is then reacted down to 3-4 psig. The additions of ethylene oxide and propylene oxide, in the same molar ratios, are repeated until the desired molecular weight is achieved. The mixture is then stripped at 100° C. to 0 psig to remove any residual oxides, after which the mixture is neutralized and dried. Diol 1 has a molecular weight of 1,480 and Diol 2 has a molecular weight of 4,740. In each of Diol 1 and Diol 2, the blocks of polyethylene glycol are no longer than 3 ethylene oxide units, while the blocks of polypropylene glycol are no longer than 7 propylene oxide units.

EXAMPLE 2

To a three neck RBF fitted with an air cooled condensor, dropping funnel, Claisen adaptor, mechanical stirring bar, nitrogen inlet and outlet with the outlet equipped with a dessicant tube is added 250 g (0.0527 mol) of Diol 2 of Example 1, 350 g of methylene chloride, and 0.45 g (0.0011 mol) of Stannous Octoate. The reactants are well stirred for forty-five minutes. To a dropping funnel is added 15.29 g (0.1055 mol) of Styrene Isocyanate and 150 g of methylene chloride. The Isocyanate mixture is added over a six to eight hour period dropwise to the diol; checking the reaction mixture occasionally for heat generated in the course of the reaction. It is imperative that the temperature of the reaction not exceed 35° C. or generally color will develop in the reaction mixture. If the temperature starts to increase the contents of the reaction mixture should be cooled by the use of an icebath. After three or four hours the completion of the reaction can be followed by IR spectroscopy by the disappearance of the hydroxyl adsorption at 3500 cm$^{-1}$. The completion of the reaction can again be followed by IR by observing the disappearance of the NCO adsorption at 2270 cm$^{-1}$. The reaction mixture is then stirred for an additional 2 hours.

The prepolymer solution is transferred to a single neck flask which is then connected to a rotary evaporator so that the methylene chloride can be removed. The stripping is done at approximately 5 mm Mercury and ambient temperature for the first hour then at 30° C. for the last thirty minutes. The prepolymer is cured at 3-5 milliwatts for thirty to ninety minutes.

EXAMPLE 3

To a three neck RBF fitted with an air cooled condensor, dropping funnel, Claisen adaptor, mechanical stirring bar, nitrogen inlet and outlet with the outlet equipped with a dessicant tube is added 250 g (0.1689) of Diol 1 of Example 1, 350 g of methylene chloride, and 0.45 g (0.0011 mol) of Stannous Octoate. The reactants are well stirred for forty-five minutes. To a dropping funnel is added 48.99 g (0.3378 mol) of Styrene Isocyanate and 150 g of methylene chloride. The Isocyanate mixture is added over a six to eight hour period dropwise to the diol; checking the reaction mixture occasionally for heat generated in the course of the reaction. It is imperative that the temperature of the reaction not exceed 35° C. or generally color will develop in the reaction mixture. If the temperature starts to increase the contents of the reaction mixture should be cooled by the use of an icebath. After three to four hours the completion of the reaction can be followed by IR spectroscopy by the appearance of the isocyanate adsorption at 1725 cm$^{-1}$ and the reduction of the hydroxyl peak. To another dropping funnel is added 15.29 g (.1055 mol) of Styrene Isocyanate which is slowly added to the reaction mixture when the hydroxyl peak and the isocyanate peak in the IR spectra have disappeared the reaction can be assumed to be complete. After the completion of the reaction 0.40% Darocur is added and the reaction mixture is then stirred for an additional 2 hours. The prepolymer solution is transferred to a single neck flask which is then connected to a rotary evaporator so that the methylene chloride can be removed. The stripping is done at approximately 5 mm Mercury and ambient temperature of the first hour then at 30° C. for the last thirty minutes. The prepolymer is cured at 3-5 milliwatts for thirty to ninety minutes.

EXAMPLES 5-7

The procedure of Example 4 is followed using the diol specified in the Table below and the amounts of reactants in the Table below.

| Ex. | Diol | sDIOL | gSI | gTDI | Ratio | mol Diol | mol SI | mol TDI | % water | Dk (multiples of HEMA) |
|---|---|---|---|---|---|---|---|---|---|---|
| 2 | 2 | 250 | 15.3 | 0 | 2:1 | .0527 | .1055 | 0 | 60 | 5 |
| 3 | 1 | 250 | 48.99 | 0 | 2:1 | .1689 | .3378 | 0 | 23 | 4 |
| 4 | 2 | 250 | 15.30 | 9.18 | 3:2 | .1055 | .1055 | .0527 | | |
| 5 | 1 | 250 | 48.99 | 29.42 | 3:2 | .3378 | .3378 | .1689 | | |
| 6 | 2 | 250 | 5.080 | 6.113 | 4:3 | .0527 | .0351 | .0351 | | |
| 7 | 1 | 250 | 16.23 | 9.61 | 4:3 | .1689 | .1126 | .1126 | | | hours the completion of the reaction can be followed by IR spectroscopy by the disappearance of the hydroxyl adsorption at 3500 cm$^{-1}$. The completion of the reaction can again be followed by IR by observing the disappearance of the hydroxyl adsorption at 3500 cm$^{-1}$. The completion of the reaction can again be followed by IR by observing the disappearance of the NCO adsorption at 2270 cm$^{-1}$. The reaction mixture is then stirred for an additional 2 hours. The prepolymer solution is transferred to a single neck flask which is then connected to a rotary evaporator so that the methylene chloride can be removed. The stripping is done at approximately 5 mm Mercury and ambient temperature for the first hour then at 30° C. for the last thirty minutes. The prepolymer is cured at 3-5 milliwatts for thirty to ninety minutes.

EXAMPLE 4

To a three neck RBF fitted with an air cooled condensor, dropping funnel, Claisen adaptor, mechanical stirring bar, nitrogen inlet and outlet with the outlet equipped with a dessicant tube is added 250 g (0.0527 mol) of Diol 2 of Example 1, 350 g of methylene chloride, and 0.45 g (0.0011 mol) of Stannous Octoate. The reactants are well stirred for forty-five minutes. To a dropping funnel is added 9.18 g (0.0527 mol) of toluene diiso cyanate (TDI) and 150 g of methylene chloride. The Isocyanate mixture is added over a two to four hour period dropwise to the diol; checking the reaction mixture occasionally for heat generated in the course of the reaction. It is imperative that the temperature of the reaction not exceed 35° C. or generally color will de-

What is claimed is:

1. A wettable, flexible, oxygen permeable, crosslinked polymer which is the polymerization product of a monomer of formula III $$L'\text{-}D\text{-}[A\text{-}L\text{-}D]_w\text{-}A\text{-}L'' \quad \text{(III)}$$

wherein w is 0-8,

L' is hydrogen, P'-B-R-B'- or P'-R-B'- in which the carbonyl group of B is bound to P', P' is hydrogen, amino, hydroxyl or a moiety containing a crosslinkable group when may be crosslinked when coreacted with a suitable crosslinking agent or when irradiated with actinic radiation;

L'' is hydrogen, -B-R-B'-P' or -B-R-P' wherein the carbonyl of B' is bound to P'; or L'' is a terminal monovalent aliphatic, aromatic or cycloaliphatic group of up to 14 carbon atoms;

each D is —O— or —NR$_7$— in which R$_7$ is hydrogen, lower alkyl or phenyl;

each L is independently -B-R-B'-, -B-R- or -R-B'-, wherein each B and B' is independently —CO—, —COO— or —CONH— with the carbonyl group thereof being linked to A or D;

each R is a divalent linking group selected from the group consisting of
  (i) an aliphatic divalent group of up to 25 carbon atoms which is uninterrupted or interrupted by an interrupting group selected from oxy, carbonyloxy, amino, aminocarbonyl, oxycarbonyl, ureido, oxycarbonylamino and carbonylimino;

(ii) a divalent-(aliphatic)$_{alpha}$-5-7-membered cycloaliphatic-(aliphatic)$_{beta}$-group wherein said non-cyclic aliphatic portions are each independently selected from the aliphatic groups set forth in (i) above, alpha and beta are each independently 0 or 1, and said group is uninterrupted or interrupted in the non-cyclic portion by an interrupting group set out in (i) above; and (iii) a divalent-(aliphatic)$_{alpha}$-aryl-(aliphatic)$_{beta}$-group having 6 to 25 carbon atoms in the aryl portion, each non-aryl portion being independently selected from the aliphatic groups set forth in (i) above, and being uninterrupted or interrupted in the non-aryl portion or between the aryl portion and the non-aryl portion by an interrupting group set forth in (i) above; each of the groups in (iii) being unsubstituted or substituted by a substituent selected from the group consisting of halogen, $C_{1-4}$alkyl and $C_{1-12}$perhaloalkyl; and each A is a copolymeric block of polyoxyalkylene, of which at least 30% of the A groups are selected from (a) homopolymer blocks of formula J

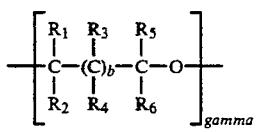

(J)

wherein b is 0 to 4, gamma is up to 15 and $R_1$ to $R_6$ are defined below; or (b) copolymer blocks of formula B

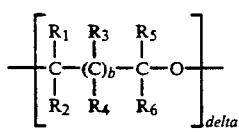

(B)

wherein b is 0 to 4, $R_1$ to $R_6$ are defined below, and delta is up to 1000 provided that within delta, there is no homopolymeric block of more than 15 oxyalkylene units, the remaining groups being homopolymers or copolymers of formula C

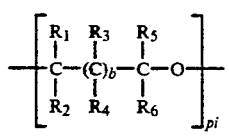

(C)

wherein b is 0 to 4 and pi is up to 1000 repeating units without regard for the size of the homopolymeric sub-blocks within pi; and wherein each of $R_1$, $R_5$ and $R_6$ are independently selected from the group consisting of hydrogen; an aliphatic, aromatic or heterocyclic radical selected from unsubstituted $C_1$-$C_6$-alkyl; substituted $C_1$-$C_{16}$-alkyl; unsubstituted $C_2$-$C_{16}$-alkenyl and substituted $C_2$-$C_6$-alkenyl; wherein the alkyl and alkenyl substituents are independently selected from the group selected from $C_2$-$C_{16}$-alkoxycarbonyl, $C_3$-$C_{16}$-alkenyloxycarbonyl, fluoro, aryl of up to 10 carbon atoms, $C_1$-$C_8$-alkoxy, $C_2$-$C_6$-alkanoyloxy, aryloxy of up to 10 carbon atoms, $C_3$-$C_6$-alkenyloxy, aroyloxy of up to 11 carbon atoms, $C_3$-$C_8$-cycloalkyl, $C_3$-$C_8$-cycloalkoxy, $C_4$-$C_8$-cycloalkylcarbonyloxy, $C_4$-$C_8$-cycloalkylcarbonyl, oxacycloalkyl of up to 7 carbon atoms, oxacycloalkoxy of up to 7 carbon atoms, oxacycloalkoxy (of up to 7 carbon atoms)-carbonyl, oxacycloalkyl (of up to 7 carbon atoms)-carbonyloxy and aryl (of up to 10 carbon atoms)-oxycarbonyl; each of said alkyl and alkenyl substituents being, in turn, optionally substituted by $C_1$-$C_6$-alkyl, fluoro or $C_1$-$C_6$-alkoxy provided said last mentioned alkoxy is not bound to a carbon atom already bound to another oxygen atom;

$R_1$, $R_2$, $R_5$ and $R_6$ are further independently aryl of up to 10 carbon atoms, $C_3$-$C_8$-cycloalkyl or oxacycloalkyl of up to 7 carbon atoms, each of said groups being unsubstituted or substituted with a substituent selected from the group of substituents for said alkyl as set forth above;

each of $R_3$ and $R_4$ is selected from the same group as set forth above for $R_1$; or $R_3$ and $R_4$ are further independently $C_2$-$C_6$-alkoxycarbonyl, $C_2$-$C_{16}$-alkanoyloxy, $C_3$-$C_{16}$-alkenoylcarbonyl or $C_3$-$C_{16}$-alkenoyloxy, each of which groups may be further substituted by fluoro, aryl of up to 10 carbon atoms or $C_1$-$C_{16}$-alkoxy; or $R_3$ and $R_4$ are further independently aryloxy of up to 10 carbon atoms, cycloalkoxy of up to 8 carbon atoms; cycloalkyl (of up to 8 carbon atoms)-carbonyloxy, cycloalkoxy (of up to 8 carbon atoms)-carbonyl, aryloxy of up to 11 carbon atoms, oxacycloalkoxy of up to 7 carbon atoms, oxacycloalkenoxy of up to 7 carbon atoms, oxacycloalkoxy (of up to 7 carbon atoms)-carbonyl, oxacycloalkyl (of up to 7 carbon atoms)-carbonyloxy, oxacycloalkenoxy (of up to 7 carbon atoms)-carbonyl or aryloxy (of up to 10 carbon atoms)-carbonyl; each of said groups may be further substituted by fluoro, $C_1$-$C_6$-alkyl or $C_1$-$C_6$-alkoxy, provided that any substituent having a oxygen atom or carbonyl group thereof as its link to the rest of the molecule may not be a substituent on the same carbon atom which is bonded to another oxygen atom; in addition two adjacent groups selected from $R_1$ to $R_6$, together with the atoms to which they are attached, may form a 5-8 membered cycloalkyl, 5-8-membered oxacycloalkyl or bicycloalkyl ring; such the resulting polymer absorbs more than 10% by weight of water when equilibrated therewith.

2. The polymer of claim 1 wherein at least 50% of said -A- groups are selected from formula J and formula B.

3. The polymer of claim 1 wherein at least 75% of said -A- groups are selected from formula A and formula B.

4. The polymer of claim 1 wherein all of said -A- groups are selected from formula J and formula B.

5. The polymer of claim 1 wherein said -A- groups are selected from formula J and formula C.

6. The polymer of claim 1 wherein said -A- groups are selected from formula B and C.

7. The polymer of claim 1 wherein each gamma is no greater than 10.

8. The polymer of claim 1 wherein each gamma is no greater than 7.

9. The polymer of claim 1 wherein each gamma is no greater than 4.

10. The polymer of claim 1 wherein each formula B has no homopolymeric subblock greater than 10 oxyalkylene units.

11. The polymer of claim 1 wherein each formula B has no homopolymeric subblock greater than 7 oxyalkylene units.

12. The polymer of claim 1 herein each formula B has no homopolymeric subblock greater than 4 oxyalkylene units.

13. The polymer of claim 1 wherein P' is a vinyl containing moiety.

14. The polymer of claim 1 wherein P' is

wherein one of $R_a$ and $R_b$ is hydrogen and the other is methyl or hydrogen.

* * * * *